(12) United States Patent
Jenkins et al.

(10) Patent No.: US 11,427,801 B2
(45) Date of Patent: Aug. 30, 2022

(54) SCATTER LABELED IMAGING OF MICROVASCULATURE IN EXCISED TISSUE (SLIME)

(71) Applicants: Case Western Reserve University, Cleveland, OH (US); UNIVERSITY HOSPITALS CLEVELAND MEDICAL CENTER, Cleveland, OH (US)

(72) Inventors: Michael W. Jenkins, Cleveland, OH (US); Yehe Liu, Cleveland, OH (US)

(73) Assignees: CASE WESTERN RESERVE UNIVERSITY, Cleveland, OH (US); UNIVERSITY HOSPITALS CLEVELAND MEDICAL CENTER, Cleveland, OH (US)

(*) Notice: Subject to any disclaimer, the term of this patent is extended or adjusted under 35 U.S.C. 154(b) by 186 days.

(21) Appl. No.: 16/761,278

(22) PCT Filed: Nov. 9, 2018

(86) PCT No.: PCT/US2018/059920
§ 371 (c)(1),
(2) Date: May 4, 2020

(87) PCT Pub. No.: WO2019/094653
PCT Pub. Date: May 16, 2019

(65) Prior Publication Data
US 2020/0283724 A1    Sep. 10, 2020

Related U.S. Application Data

(60) Provisional application No. 62/583,645, filed on Nov. 9, 2017.

(51) Int. Cl.
*G06T 7/136* (2017.01)
*C12N 5/00* (2006.01)
(Continued)

(52) U.S. Cl.
CPC ......... *C12N 5/0018* (2013.01); *C12N 5/0679* (2013.01); *C12N 5/0691* (2013.01);
(Continued)

(58) Field of Classification Search
CPC .. C12N 5/0018; C12N 5/0679; C12N 5/0691; C12N 2513/00; G01N 21/4795;
(Continued)

(56) References Cited

U.S. PATENT DOCUMENTS 8,030,459 B2 * 10/2011 Papisov ................. A61K 47/61
536/25.31
9,600,885 B2 * 3/2017 Nempont ............... A61B 6/481
(Continued)

OTHER PUBLICATIONS

Liu, Yehe, et al. "SLIME: scattering labeled imaging of microvasculature in excised tissues using OCT (Conference Presentation)." Optical Coherence Tomography and Coherence Domain Optical Methods in Biomedicine XXI. vol. 10053. International Society for Optics and Photonics, 2017.
(Continued)

*Primary Examiner* — Ali Bayat
(74) *Attorney, Agent, or Firm* — Tarolli, Sundheim, Covell & Tummino LLP

(57) ABSTRACT

The present disclosure relates to a simple, fast, and low cost method for 3D microvascular imaging, termed "scatter labeled imaging of microvasculature in excised tissue" (SLIME). The method can include perfusing a contrast agent through vasculature of a tissue sample with a contrast perfusing unit (22). The contrast agent can include colloids and a dispersant. After the contrast agent is perfused through the vasculature, the vasculature of the tissue sample can be treated with a cross-linking agent delivery unit (24) providing a molecule that cross links with at least a portion of the dispersant to form a sticky, non-Newtonian polymer that prevents leakage of the contrast agent out of the vasculature
(Continued)

of the tissue sample. The tissue sample can then be immersed in a solution comprising a clearing agent with an optical clearing unit (26) and subsequently imaged.

16 Claims, 8 Drawing Sheets

(51) Int. Cl.

| | | |
|---|---|---|
| *G06T 7/11* | (2017.01) | |
| *C12N 5/071* | (2010.01) | |
| *G01N 21/47* | (2006.01) | |
| *G01N 21/49* | (2006.01) | |
| *G01N 33/483* | (2006.01) | |
| *G06T 5/00* | (2006.01) | |
| *G06T 5/20* | (2006.01) | |
| *G06T 5/50* | (2006.01) | |
| *G06T 7/00* | (2017.01) | |

(52) U.S. Cl.
CPC ......... *G01N 21/4795* (2013.01); *G01N 21/49* (2013.01); *G01N 33/4833* (2013.01); *G06T 5/002* (2013.01); *G06T 5/009* (2013.01); *G06T 5/20* (2013.01); *G06T 5/50* (2013.01); *G06T 7/0012* (2013.01); *G06T 7/11* (2017.01); *G06T 7/136* (2017.01); *C12N 2513/00* (2013.01); *G06T 2207/10101* (2013.01); *G06T 2207/20224* (2013.01); *G06T 2207/30024* (2013.01)

(58) Field of Classification Search
CPC .... G01N 21/49; G01N 33/4833; G06T 5/002; G06T 5/009; G06T 5/20; G06T 5/50; G06T 7/0012; G06T 7/11; G06T 7/136; G06T 2207/10101; G06T 2207/20224; G06T 2207/30024; G06T 2207/20032; G06T 2207/20044; A61B 5/0066; A61B 5/02007
USPC .......................................................... 382/131
See application file for complete search history.

(56) References Cited

U.S. PATENT DOCUMENTS

| | | | |
|---|---|---|---|
| 2004/0101088 A1* | 5/2004 | Sabol | A61B 6/481 378/4 |
| 2010/0145185 A1* | 6/2010 | Hong | A61B 5/7257 600/420 |
| 2014/0236004 A1* | 8/2014 | Rognin | A61B 8/5223 600/431 |
| 2016/0075822 A1* | 3/2016 | Yang | C08G 18/4646 525/440.06 |

OTHER PUBLICATIONS

PCT International Search Report and Written Opinion for corresponding International Application Serial No. PCT/US2018/059920, dated Feb. 12, 2019, pp. 1-14.

\* cited by examiner

SCATTER LABELED IMAGING OF MICROVASCULATURE IN EXCISED TISSUE (SLIME)

RELATED APPLICATION

This application claims priority to U.S. Provisional Application Ser. No. 62/583,645, filed Nov. 9, 2017, entitled "A POSTMORTEM 3D MICROVASCULATURE IMAGING METHOD USING OPTICAL COHERENCE TOMOGRAPHY", the entirety of which is hereby incorporated by reference for all purposes.

GOVERNMENT FUNDING

This invention was made with government support under HL126747 and HL083048 awarded by the National Institutes of Health. The government has certain rights in the invention.

TECHNICAL FIELD

The present disclosure relates generally to three-dimensional (3D) imaging of the microvasculature and, more specifically, to a simple, fast, and low cost method for 3D microvascular imaging, termed "scatter labeled imaging of microvasculature in excised tissue" (SLIME).

BACKGROUND

Abnormal microvascular organization can be a sign of disease. In recent years, various 3D microvascular mapping methods (e.g., micro-CT, microscopy with serial slicing, confocal microscopy) have provided valuable information about the structure and function in various tissues and disease states. Unfortunately, many of these methods are either complex, expensive, and/or time intensive. These 3D microvascular mapping methods are not optimal for applications or studies involving both large volumes and large sample populations (e.g., studies involving diverse phenotypes, drug screening, etc.).

SUMMARY

In an aspect, the present disclosure can include a simple, fast, and low cost method for 3D microvascular imaging, termed "scatter labeled imaging of microvasculature in excised tissue" (SLIME). SLIME is based on optical coherence tomography (OCT), benefitting from the high speed, high resolution, wide field of view (FOV), and low cost of OCT. SLIME broadens the vascular imaging capability of OCT through use of an OCT contrast agent and optical cleansing.

The method can include perfusing vasculature of a tissue sample with a contrast agent. The contrast agent can include a colloid and a dispersant. After the contrast agent is perfused through the vasculature, the tissue sample can be treated with chemicals that cross-link with at least a portion of the dispersant to form a sticky, non-Newtonian polymer that prevents leakage of the contrast agent out of the vasculature of the tissue sample. The tissue sample can then be immersed in a solution comprising an optical clearing agent. After a time, in some instances, the cleared tissue sample can be imaged (e.g., using OCT) to collect volumetric image data, then the collected image data can be processed and analyzed.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Figure 1:
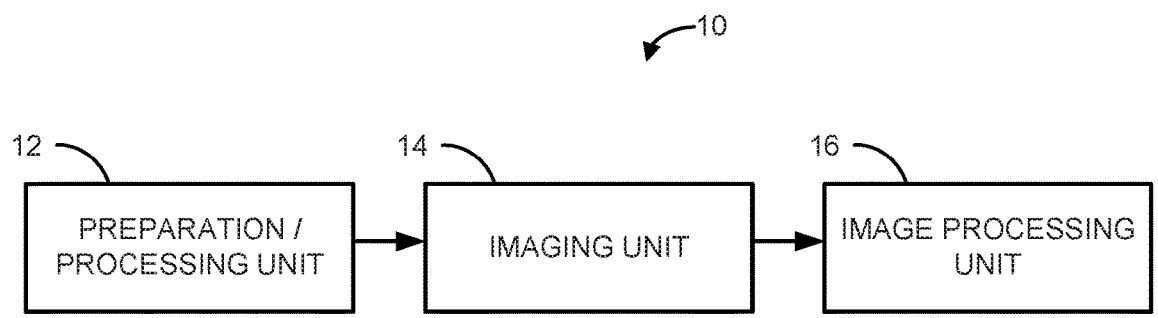
FIG. 1 is a diagram showing a system that can be used to perform scatter labeled imaging of microvasculature in excised tissue (SLIME) in accordance with an aspect of the present disclosure.

Unless otherwise defined, all technical terms used herein have the same meaning as commonly understood by one of ordinary skill in the art to which the present disclosure pertains.

As used herein, the singular forms "a," "an" and "the" can also include the plural forms, unless the context clearly indicates otherwise.

As used herein, the terms "comprises" and/or "comprising," can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

As used herein, the terms "first," "second," etc. should not limit the elements being described by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "imaging" can refer to the act of creating a visual representation of an interior of at least a portion of a sample for analysis. For example, the sample can be tissue that has been excised or removed from a subject's body (or "excised tissue"). When the imaging is referred to as being "three-dimensional (3D)", a volumetric visual representation of the interior of at least the portion of the sample is created.

As used herein, the term "optical coherence tomography (OCT)" can refer to an imaging technique that uses coherent light to capture micrometer resolution, two- and three-dimensional images from within a sample by optical scattering. OCT is based on low-coherence interferometry, typically employing light with visible to near-infrared wavelengths that penetrates into the scattering medium.

As used herein, the term "microvasculature" can refer to the smallest vessels of the circulatory system (e.g., arterioles, venules, capillaries, or the like) that delivers blood into tissue. The vessels of the microvasculature can average, for example, 0.3 millimeters in diameter or less. As an example, the sample can include microvasculature within excised tissue.

As used herein, the term "scatter labeled imaging of microvasculature in excised tissue (SLIME)" can refer to a convenient and cost effective method for evaluating microvascular morphology and organ-level microvascular organization. SLIME is operational over large fields of view (FOVs) in large cohort studies in a variety of excised tissue samples from a variety of subjects. SLIME generally includes the steps of tissue preparation and processing (e.g., delivering a contrast agent, cross-linking the contrast agent to prevent leakage, and optical clearing the sample), imaging, and data processing.

As used herein, the term "contrast agent" can refer to a substance used to increase the visibility of a structure (e.g., blood vessels, gastrointestinal tissue, lymphatic tissue, etc.) within the sample being imaged. Contrast agents can be classified based on the imaging modalities in which they are being used. The contrast agent can be formed of a colloid and a dispersant.

As used herein, the term "colloid" can refer to a mixture in which one substance of microscopically dispersed insoluble particles is suspended throughout another substance. For example, the insoluble particles can include $TiO_2$ and the other substance can be a water-based solution.

As used herein, the term "dispersant" can refer to a surfactant polymer or other substance added to a colloid suspension to improve the separation of particles and to prevent settling or clumping. As an example, the dispersant can be polyvinyl alcohol/acetate (PVA).

As used herein, the term "slime" can refer to a sticky, non-Newtonian polymer formed by contacting a cross-linking solution (e.g., containing boric acid) with a dispersant.

As used herein, the terms "cross-linking" and "crosslinking" can refer to the act of creating a chemical bond (e.g., covalent or ionic) that links one polymer chain to another. Cross-linking can change the material properties of the linked polymer molecules.

As used herein, the terms "optical clearing" and "clearing" can refer to the act of minimizing light scatter from a sample by exposing the sample to a clearing agent. For example, the sample can be immersed in a modified CUBIC-I clearing agent containing boric acid to clear the sample for imaging.

As used herein, the term "subject" can be used interchangeably and refer to any warm-blooded organism including, but not limited to, a human being, a pig, a rat, a mouse, a bird, a dog, a cat, a goat, a sheep, a horse, a monkey, an ape, a rabbit, a cow, etc.

II. Overview

The present disclosure can include a simple, fast, and low cost method for 3D microvascular imaging, termed "scatter labeled imaging of microvasculature in excised tissue" (SLIME). SLIME is an integrated method with tissue processing, imaging and data processing. SLIME is both a convenient and cost effective method for evaluating microvascular morphology over a large FOV in large cohort studies. However, SLIME can be applied to any biological vessels or lumens that can be perfused (e.g., lymphatic tract, digestive tract, etc.).

As an example, SLIME can be used with optical coherence tomography (OCT) (however, other imaging modalities can be used with the only change being a different colloidal-based contrast agent). As such, the vasculature can be filled with a specialized OCT contrast agent to produce a strong OCT signal. The contrast agent is rapidly cross-linked to prevent leakage. The tissue is optically cleared to reduce light scattering and increase the accessible imaging depth. Because the contrast agent is not affected by optical clearing, the combined effect generates high OCT contrast between the filled vasculature and the rest of the tissue. Effective 3D image processing specific for SLIME allows visualization and quantification of microvascular morphology. The overall SLIME pipeline allows users to obtain 3D microvascular maps of small animal organs with minimal operation time.

III. Systems

One aspect of the present disclosure can include a system 10 (FIG. 1) that can be used to perform scatter labeled imaging of microvasculature in excised tissue (SLIME). The imaging modality used in connection with SLIME can be optical coherence tomography (OCT), but other imaging modalities can be utilized with only minimal changes to the SLIME procedure. SLIME provides a convenient and cost effective way to evaluate properties (e.g., morphology, 3D organization, etc.) of a component within an excised tissue sample. The component can include any biological vessels or lumens that can be perfused (e.g., lymphatic tubes, blood vessels (e.g., micro vessels), the digestive tract, and the like). SLIME can provide high-resolution images with a wide field of view (FOV) and imaging depth at a high speed without suffering from shadowing artifacts.

The system 10 includes a preparation/processing unit 12, an imaging unit 14, and an image processing unit 16. One or more of the preparation/processing unit 12, the imaging unit 14, or the image processing unit 16 can perform computer-aided actions, which are stored in one or more non-transitory memory units and executed by one or more processors. In some instances, each of the preparation/processing unit 12, the imaging unit 14, and the image processing unit 16 can be unique entitles (e.g., located at different places). However, in other instances, functionalities of one or more of the preparation/processing unit 12, the imaging unit 14, and the image processing unit 16 can be combined.

Figure 2:
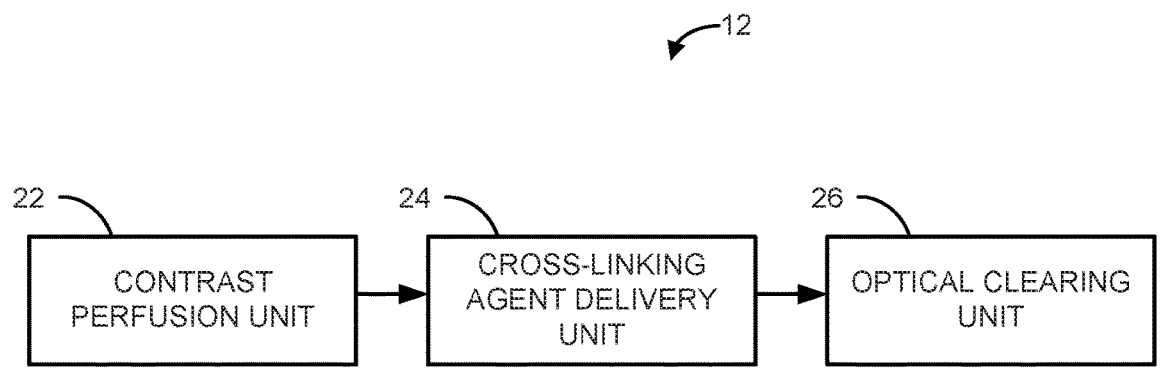
FIG. 2 is a diagram showing an example configuration of the preparation/processing unit in FIG. 1.

The preparation/processing unit 12 can broaden the imaging capability of OCT and other imaging modalities by combining the use of a contrast agent with optical clearing. FIG. 2 shows an example preparation/processing unit 12, including a contrast perfusion unit 22, a cross-linking agent delivery unit 24, and an optical clearing unit 26 that work together to prepare the sample for imaging by the imaging unit 14.

The contrast perfusion unit 22 can fill the component of the tissue sample with a contrast agent. The tissue sample can be excised or can be in a natural state inside the subject's body pre-excision. The contrast agent maintains a low viscosity necessary for perfusion of the contrast agent through the component of the tissue sample. As an example, the contrast agent can include a colloid and a dispersant. For example, the colloid can be chosen to provide a strong signal based on the imaging modality being used (e.g., when the imaging modality is OCT, the colloid and dispersant can be chosen to produce a strong OCT signal) and the dispersant can be chosen to maintain the low viscosity. As an example, when the imaging modality is OCT, the colloid can include $TiO_2$ nanoparticles in a water-based solution (which can optimize backscattering), while the dispersant can include low molecular weight (e.g., Mw ~10,000) polyvinyl alcohol/acetate (PVA) (which can optimize viscosity). In some instances, the contrast agent can include a preservative for longer preservation, like paraformaldehyde (PFA).

While perfusion with the contrast agent requires low viscosity, keeping the contrast agent within the component of the tissue sample requires low fluidity. Accordingly, after perfusion with the contrast agent, the tissue sample can be treated with a cross-linking agent to lower the fluidity. The tissue sample can be excised or can be in a natural state inside the subject's body pre-excision. Accordingly, the preparation/processing unit 12 can also include a cross-linking agent delivery unit 24 to deliver the cross-linking agent to the component of the tissue sample.

At least a portion of the cross-linking agent delivered by the cross-linking agent delivery unit 24 can rapidly cross-link to a portion of the binding agent of the contrast agent. The cross-linking agent can include borate ions, which can cross-link with the dispersant of the contrast agent within a few seconds to form a sticky, non-Newtonian polymer that clogs any openings in the component of the tissue sample, such as those openings that may have been created during the excision procedure, to prevent contrast agent leakage.

Additionally, the preparation/processing unit can include an optical clearing unit 26, which can perform optical clearing on an excised tissue sample for a time that varies based on a size of the excised tissue sample. The optical clearing unit 26 can aid in the clearing with a mechanical force, like gentle shaking. To perform the optical clearing, the excised tissue sample is immersed in a clearing agent (e.g., CUBIC-1 for OCT imaging to reduce light scattering and increase the accessible imaging depth, but different clearing agents can be used) that has been modified to contain boric acid. Optical clearing is simple and fast, requiring only the immersion of the excised tissue sample in the clearing agent that has bene modified to contain boric acid. The clearing agent can generate sufficient transparency for imaging, while borate ions of the boric acid further stabilize the contrast agent inside the excused tissue sample. Because the contrast agent is not affected by the optical clearing, the combined effect generates high contrast between the filled component and the rest of the tissue sample.

Referring again to FIG. 1, the imaging unit 14 can record raw data corresponding to one or more images of the excised tissue sample after the excised tissue sample emerges from the preparation/processing unit. As an example, the imaging unit 14 can record the one or more images of the excised tissue sample while immersed within the clearing agent modified with boric acid. In some instances, the imaging unit 14 can record one or more OCT images of the excised tissue sample. However, other imaging modalities can be utilized by the imaging unit 14.

The image processing unit 16 can receive the raw data from the imaging unit 14 and process the raw data to provide information about the images and/or the images themselves. The raw data can provide high contrast images of the component of the excised tissue sample. For example, the image processing unit 16 can employ one or more image processing tools, such as ImageJ, Almira, or the like, to provide visualization and/or quantitate information about the one or more images that can be used for statistical analysis.

As an example, the image processing unit 16 can perform the following processing on OCT raw data. A multi-iterative 3D median filter can be applied to the raw data to reduce speckle noise. Coherence enhancing diffusion filtering can be applied to reduce noise and improve continuity of the component of the tissue sample. Image contrast and intensity uniformity can be further improved by background subtraction and 3D unsharp filtering. In addition to qualitative visual interpretation, processed data can be segmented through simple intensity thresholding and skeletonized into 3D graphical data for quantitative analysis. Topological assessments (e.g., skeletonization) can be readily performed with existing software tools.

IV. Methods

Another aspect of the present disclosure can include methods 30 and 40 (FIGS. 3 and 4) for performing scatter labeled imaging of microvasculature in excised tissue (SLIME). SLIME provides a convenient and cost effective way to evaluate properties (e.g., morphology, 3D organization, etc.) of a component within an excised tissue sample. The component can include any biological vessels or lumens that can be perfused (e.g., lymphatic tubes, blood vessels (e.g., micro vessels), the digestive tract, and the like). SLIME can provide high-resolution images with a wide field of view (FOV) and imaging depth at a high speed without suffering from shadowing artifacts. The methods 30 and 40 can be executed using at least a portion of the system 10 shown in FIGS. 1 and 2 and described above.

Figure 3:
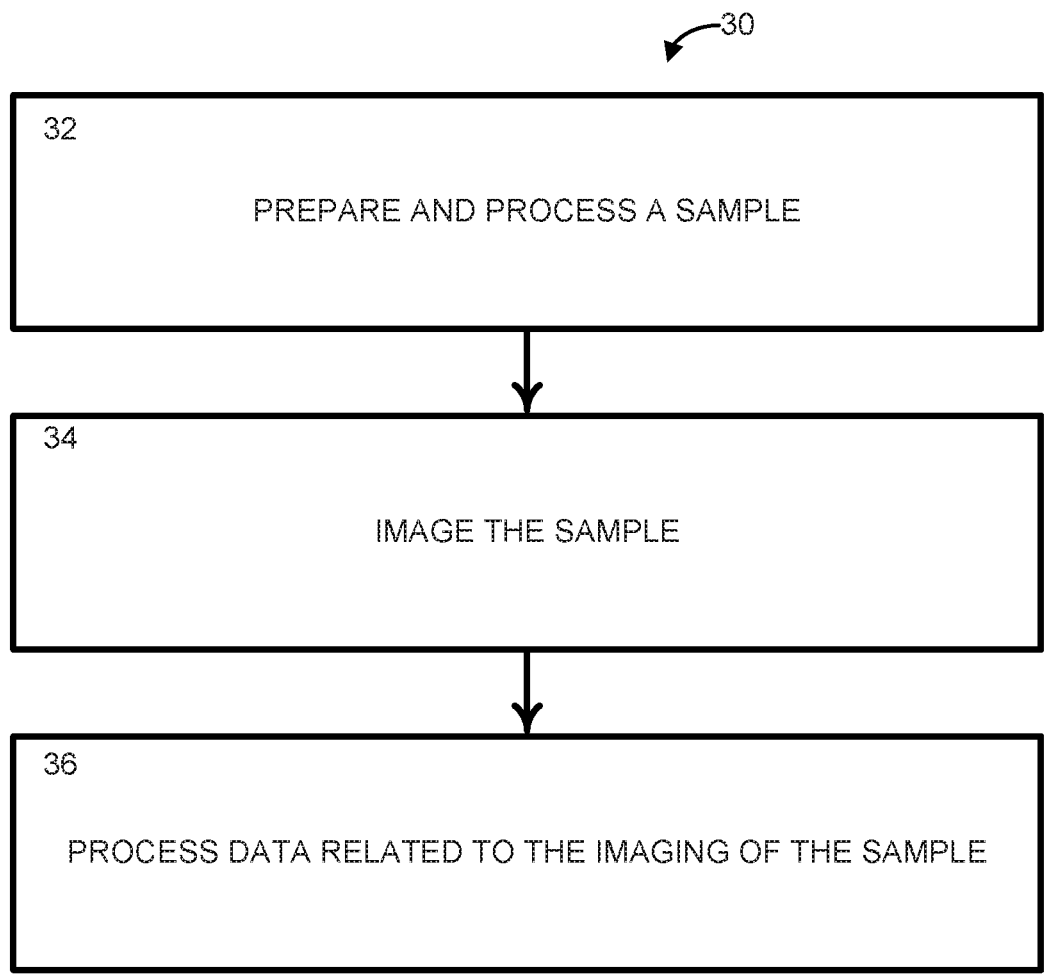
FIG. 3 is a process flow diagram illustrating a method for performing SLIME according to another aspect of the present disclosure.
Figure 4:
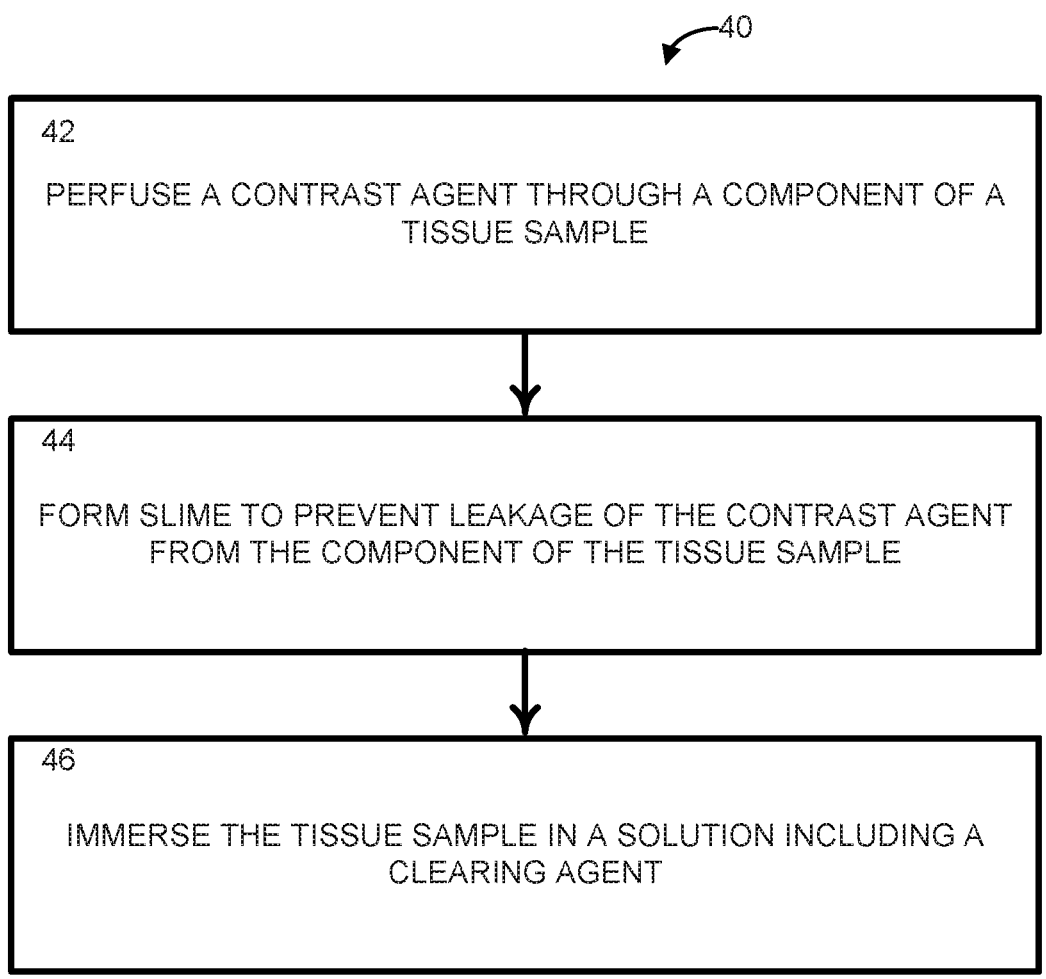
FIG. 4 is a process flow diagram illustrating an example method for preparing and processing a sample for the SLIME procedure in FIG. 3.

Referring now to FIG. 3, illustrated is a process flow diagram of a method 30 for performing SLIME according to another aspect of the present disclosure. As noted, the imaging modality used in connection with SLIME can be optical coherence tomography (OCT), but other imaging modalities can be utilized with only minimal changes to the SLIME procedure. At step 32, a sample can be prepared and processed to broaden the imaging capability of OCT and other imaging modalities by combining the use of a contrast agent with optical clearing. The preparation and processing of the sample can include the steps of the method 40 illustrated in FIG. 4.

At step 42, a component of the tissue sample can be perfused with a contrast agent to fill the component of the tissue sample with the contrast agent. The tissue sample can be excised or can be in a natural state inside the subject's body pre-excision. The contrast agent maintains a low viscosity necessary for perfusion of the contrast agent through the component of the tissue sample. As an example, the contrast agent can include a colloid and a dispersant. For example, the colloid can be chosen to provide a strong signal based on the imaging modality being used (e.g., when the imaging modality is OCT, the colloid and dispersant can be chosen so that the component produces a strong OCT signal) and the dispersant can be chosen to maintain the low viscosity. As an example, when the imaging modality is OCT, the colloid can include $TiO_2$ nanoparticles in a water-based solution (which can optimize backscattering), while the dispersant can include low molecular weight (e.g., Mw ~10,000) polyvinyl alcohol/acetate (PVA) (which can optimize viscosity). Different colloids and/or dispersants can be chosen for different imaging modalities. In some instances, the contrast agent can include a preservative for longer preservation, like paraformaldehyde (PFA).

After perfusion with the contrast agent, at step 44, the component of the tissue sample (either excised or in a natural state) can be treated with a cross-linking agent to ensure low fluidity to keep the contrast agent within the component of the tissue sample. The cross-linking agent can rapidly cross-link with at least a portion of the dispersant to form a sticky, non-Newtonian polymer that closes any openings in the component of the tissue sample and prevents leakage of the contrast agent out of the component of the tissue sample.

At step 46, the tissue sample can be immersed in a solution comprising a clearing agent. The clearing agent can include a traditional clearing agent (CUBIC-1 for OCT imaging) that has been modified to contain boric acid. Optical clearing is simple and fast, requiring only the immersion of the excised tissue sample in the clearing agent that has bene modified to contain boric acid. The clearing agent can generate sufficient transparency for imaging, while borate ions of the boric acid further stabilize the contrast agent inside the excused tissue sample. Because the contrast agent is not affected by the optical clearing, the combined effect generates high contrast between the filled component and the rest of the tissue sample.

Referring again to FIG. 3, at step 34, the prepared and processed sample can be imaged. When the sample is imaged, raw data corresponding to one or more images of the sample immersed in the clearing agent solution can be recorded. At step 36, raw data related to the imaging of the sample can be processed. The processing can enable assessing whether a disease state exists in the sample and/or quantifying aspects of morphology of the component of the tissue sample based on analyzing the images of the tissue sample. The analysis can be performed according to an image processing procedure.

An example when the imaging unit records OCT raw data, the processing can include one or more of the following. A multi-iterative 3D median filter can be applied to the raw data to effectively reduce speckle noise. Coherence enhancing diffusion filtering can be applied to reduce noise and improve continuity of the component of the tissue sample. Image contrast and intensity uniformity can be further improved by background subtraction and 3D unsharp filtering. In addition to qualitative visual interpretation, processed data can be segmented through simple intensity thresholding and skeletonized into 3D graphical data for quantitative analysis. Topological assessments (e.g., skeletonization) can be readily performed with existing software tools.

V. Experimental

The following experiment shows a simple, fast, low cost three-dimensional (3D) microvascular mapping method, which uses optical coherence tomography (OCT), and is referred to as "scatter labeled imaging of microvasculature in excised tissue" (SLIME). SLIME combines optical clearing with a scatter-based OCT contrast agent, greatly extending the OCT imaging depth in excised tissues, while maintaining a simple and lost cost approach that does not require extensive knowledge of OCT. The following experimental results are shown for the purpose of illustration only and are not intended to limit the scope of the appended claims.

Method

Steps of SLIME

First, the SLIME contrast agent was formulated to optimize both its backscattering and viscosity parameters. While perfusion requires low velocity, keeping the contrast agent in the blood vessel requires low fluidity. After perfusion, treat tissue with a sticky non-Newtonian polymer (referred to as the toy "Slime") to clog any vessel openings and effectively prevent contrast agent leaking. After clogging any vessel openings, the tissue/organ is harvested and immersed in an optical clearing solution. The optical clearing solution generates sufficient transparency for OCT imaging. Additionally, the optical clearing solution can further stabilize the contrast agent in the tissue/organ. After clearing, the sample can be imaged directly in the clearing solution with conventional OCT. The microvasculature organization can be reflected through intensity contrast directly in a single scan.

SLIME Contrast Agent

The contrast agent stock solution was a mixture of 12.5% w/w titanium dioxide ($TiO_2$) nanoparticles, 12.5% w/w polyvinyl alcohol/acetate (PVA), 0.5% w/w glycerol and 2.5% w/w commercial paint wetting agent in water. The concentration of each ingredient can be adjusted to achieve different image contrast and solution viscosity. To prevent aggregation of $TiO_2$ nanoparticles in PVA solution, concentrated $TiO_2$ water colloid and PVA solution were prepared separately and mixed to make the final colloid solution just before use. A commercial water-based paint wetting agent (Solsperse 27000, Lubrizol) is diluted before adding $TiO_2$ nanoparticles (Aerosil Aeroxide P25, Evonik, anatase, primary particle size =21 nm) to make a 25% w/w colloid solution. For each gram of $TiO_2$ nanoparticles, 200 mg of wetting agent was used. After gentle stirring using a magnetic stirrer, the mixture is sonicated using a 250 W, 20 kHz, ultrasound homogenizer. Sonication at full power for 1 minute is sufficient to disperse 25 g of $TiO_2$ nanoparticles in 5 g of wetting agent dissolved in 70 g of water. Low molecular weight PVA ($M_w$, 9000-10000, Sigma, 80% hydrolyzed) was dissolved in deionized water at 80° C. under constant stirring to make a 25% w/w solution. The 25% $TiO_2$ colloid is mixed 1:1 with the 25% PVA solution at 80° C. 0.5 w/w glycerol is added to the mixture as a plasticizer. The mixture was further sonicated for 1 min per 100 g of mixture. The final colloidal solution should be very stable and have a shelf life of more than 3 months. If small amounts of precipitation occur during storage, sonication can be used to re-disperse the constituents. The stock solution was diluted 4:1 in 5× phosphate buffered saline (PBS) or 20% paraformaldehyde (PFA) to make a working solution.

Crosslinking Solution

4% w/v boric acid was used as the crosslinking solution. The pH of the solution was titrated to 7.8 with 1 N sodium hydroxide. The solution was stored at 37° C. Precipitation gradually occurs when the temperature is lower than the storage temperature, but will not significantly affect the performance of crosslinking. 0.05% w/v $NaN_3$ may be added as a microbicide for longer storage time.

Clearing Solution

The clearing solution was modified from the Scale CUBIC-1 clearing agent, which contains 25% w/w urea, 25% w/w Quadrol, 15% w/w Triton-X100, 15% w/w crosslinking solution and 15% w/w water. 25% w/w glycerol can be used as an alternative to Quadrol. To prepare 100 g clearing solution, 25 g Quadrol and 15 g crosslinking solution were dissolved in 15 mL DI water with continuous stirring using a magnetic stirrer hotplate. Heating or 20 kHz sonication can be applied to accelerate the solubilization, but the temperature of the solution should be maintained below ~50° C. After the solution was completely mixed, 25 g of urea was added and dissolved by continuous stirring. The solution was cooled to room temperature and weighed. To compensate for the evaporation during the previous steps, DI water is added to make the total mass of the solution 85 g. Then 15 g of Triton X-100 is added and stirred slowly at room temperature until completely mixed. The solution can be stored at room temperature for up to 3 months.

Perfusion

Prior to perfusion, a working solution was made by mixing the SLIME contrast agent stock solution 4:1 with 5× PBS or 20% PFA. The mixture was gently shaken for 5 minutes with a nutating mixer. Vigorous shaking should be avoided to prevent air bubble formation. In general, the perfusion protocol is identical to generic perfusion fixation protocols except the fixative solution is replaced with the SLIME contrast agent. Several small modifications to the SLIME perfusion protocol are needed to accommodate different animal models and tissues of interest. For embryos from smaller animals (e.g., mouse, avian), the animal can be perfused directly with the working solution. For larger animals (e.g., adult mouse and rat), the vasculature should be first flushed with anticoagulation solutions such as heparinized saline. The left ventricle is a convenient cannulation site for SLIME perfusion. Alternatively, if intact coronary circulation is being studied, perfusion can be done at the aortic arch or abdominal aorta. Because the contrast agent is white, the endpoint of perfusion is easily observed at low magnification. The tissues of interest turn pale and the large vessels become distinctly white. After perfusion, the tissues of interest are rinsed using the borate crosslinking solution. For tissues buried under other structures (e.g., brain under the skull), the crosslinking solution can be injected into the interfaces and cavities near the tissue using a syringe. After a brief waiting period of about 30 s, the tissues can be dissected out of the body using appropriate tools and procedures. As the tissues are surrounded by the crosslinking agent, the contrast agent rapidly turn into a viscous and sticky material, which occludes vessels once the dissection takes place. If the vessels are pressurized or crosslinking is insufficient, leaking of contrast agent may occur. Adding more crosslinking agent with gentle compression can effectively stop the leakage. If contrast agent collects on the sample surface and impedes sample handling (e.g., sticks to the instruments), the contrast agent on the sample surface can be hardened and peeled off with a brief rinse of formamide Optical Clearing After dissection, samples were cleared by immersing in excess modified Scale CUBIC-I solution. Clearing time depends on the size of the sample with bigger samples taking significantly longer to clear. For instance, a stage 36 quail embryo heart (~2.5×4×4 mm) only requires about 12 hours to clear. The brain from the same stage quail embryo (~3.5×8×8 mm) requires more than 24 hours to clear. It can take more than 5 days to clear the brain of a P5 mouse (~6×12×12 mm). To reduce the time for clearing large tissue samples, the samples can be dissected into ~2 mm thin slices using a vibratome, which reduces the clearing time to less than 24 hours. For faster clearing speed, the clearing solution can be replaced with fresh solution every 2 hours.

OCT Imaging

The cleared SLIME sample can be directly imaged using conventional OCT. The sample was immersed in optical clearing solution during OCT imaging. To eliminate reflection from the curved liquid-air interface, a microscope coverslip was placed on top of the sample. Because the light was polarized, signal from the cleared tissue can be suppressed by cross-polarizing the light between the sample arm and the reference arm. In contrast, $TiO_2$ nanoparticle clusters depolarize the light, and therefore are not strongly affected by the cross-polarization. Since the intensity ratio between the contrast agent and the cleared tissue was high with this simple setup, sufficient image contrast can be obtained with just a single volume scan. Conventional OCT with Gaussian focusing only has the optimal lateral resolution in the Rayleigh range. As focal power increases, resolution increases and depth of focus decreases. With conventional OCT, both large axial range and high resolution can be achieved through volume stitching. In this case, multiple volume scans should be taken by focusing the beam at different depths of the tissue. Alternatively, OCT with Bessel beam illumination could be used with SLIME to achieve both high resolution and extended depth in single scans.

Data Processing and Analysis

Because SLIME raw data provides high contrast images of blood vessels, simple automated image processing can be performed to compute useful information using tools that are readily available. For example, a multi-iterative 3D median filter can be applied to reduce speckle noise. Coherence enhancing diffusion filtering can be applied to further reduce noise and improve vessel continuity. Image contrast and intensity uniformity can be further improved by background subtraction and 3D unsharp filtering. In addition to qualitative visual interpretation, processed vascular data can be segmented through simple intensity thresholding and skeletonized into 3D graph data for quantitative analysis. Topological assessments (e.g., skeletonization) can be readily performed with existing tools (e.g., Amira).

In this case, data was processed using customized code and image processing software. Conventional OCT processing (e.g., wavenumber linearization, Fourier transform) was performed on SLIME raw data to make typical OCT structure images. For higher image contrast, log compression can be omitted. If necessary, regions of interest are manually segmented to minimize processing time before further image processing. Some quantitative data analysis, such as cross-sectional area and circumference of large vessels can be performed directly without further image processing. To perform vessel cross-sectional area or circumference calculations, orthogonal slices to a vessel of interest are selected and the area or circumference are manually segmented and computed with Fiji (ImageJ).

Additional processing of the SLIME images was performed to reduce noise and improve data interpretability after log compression. First, 3 iterations of a 3D median filter were applied to reduce noise. Next, the data were filtered with a 3D coherence-enhancing diffusion filter to remove gaps in the vessel caused by OCT speckle noise. These filters were anisotropic and smooth along the length of linear structures (e.g., vessels) which effectively reduces speckle noise and enhances vessel connectivity, which improves the ease of visual interpretation and automated vessel segmentation. Occasionally, samples were not sufficiently cleared and background subtraction is used. In this situation, background is estimated with a down-sampled, blurred image. To further improve vessel contrast, the data are processed using either an unsharp mask or high pass filter.

In this work, data skeletonization was performed with Amira (Thermo Fisher Scientific). One of the most frequently used visualization methods demonstrated in this manuscript is referred to as "volume rendering"—a ray tracing based rendering technique that simulates the voxels of 3D objects as solid matter. Different voxel values are mapped to different optical properties. Usually larger voxel values are simulated as more solid and scattering materials, while smaller values are more transparent. A simulated light source casts rays onto the objects, creating reflections, diffusions and shadows to form an image. Volume rendering is most suitable for studying vessel morphology near the surface. For visualizing internal structures deep in the volume, the sample can be cropped/clipped into smaller/thinner volumes.

To get a binary map of the vasculature for skeletonization, simple intensity-based thresholding was used. With skeletonized data, local lengths, locations and orientations of local vessel segments can be evaluated and used to calculate other parameters such as vessel length density and local tortuosity. Here, vessel length density is defined and calculated by counting the total length of the vessel in a unit volume of tissue. Because vessel diameter can vary significant due to preparation and measurement errors, we believe vessel length density is a better measurement of vessel density compared to volume fraction.

Animals

According to IACUC guidelines at Case Western Reserve University, the policy on the use of Avian Embryos states that, "If embryos will be sacrificed prior to 3 days before hatching, the research will not be subject to IACUC review." Domestic quail embryos typically hatch around embryonic day 17. Therefore, IACUC approval was not required for quail embryos in this study. Fresh fertilized quail eggs were purchased from a commercial supplier. The eggs were incubated in an egg incubator at 37° C. with near saturated humidity, until they achieved the desired developmental stages.

For the preliminary tests on rodents, all procedures were conducted in accordance with Case Western Reserve University IACUC-approved protocols. All rodents were leftover wild type animals from unrelated studies. The rodents were euthanized by perfusion fixation under anesthesia prior to SLIME perfusion.

Quail Fetal Alcohol Syndrome (FAS) Model

The primary reason to use the quail FAS animal model was to help validate the technique. The FAS model was easy to use and causes a large variety of cardiovascular structural abnormalities at different scale levels. It was hypothesized that some abnormalities could also occur at the microvascular level, and would be diverse in their presentation. The goal of the work was to demonstrate SLIME's ability to identify microvascular abnormalities that may be missed using traditional techniques.

To generate quail embryos with FAS, a well-established protocol was used. In brief, quail eggs were incubated at 37° C. until gastrulation (~21 hours). The eggs were then injected with 40 µl of 50% ethanol in normal saline solution. The injection sites were sealed, and the eggs were kept in the incubator until they reached the desired developmental stages.

To validate SLIME's ability to capture microvascular phenotypes across an entire organ, the SLIME results of 6 normal quail embryo hearts and 6 quail embryo hearts from the FAS model were compared. The coronary patterns from the SLIME data were evaluated by a human expert.

To demonstrate SLIME's ability to make quantitative measurements, some stage 36 quail embryo brains from both groups were examined Because the brains have large volume, diverse vascular morphology and high structural symmetry, they were ideal for validating and demonstrating quantitative assessment. Vessel length density, length to specific points and local tortuosity measurements were performed. Using the symmetry of the brain, the measurements were validated by comparing analysis made on both sides of the brain.

Results

SLIME is a convenient and cost effective method for evaluating microvascular morphology over a large FOV in large cohort studies in a variety of animal tissues (including those of rodents). SLIME broadens the vascular imaging capability of OCT and provides the benefits of high speed, high resolution, and a wide FOV. Even in a slow OCT system with 10 kHz line rate, it takes less than 2 minutes to acquire a 4×4×3 FOV (XYZ) at 4×4×6 µm voxel sampling, which is sufficient to resolve the organization of the microvasculature in most tissues tested. Further, SLIME does not have shadowing artifacts that are common in OCT and the imaging depth is much greater and only limited by the optics of the OCT system (~2 mm/single scan for capillary resolution).

Figure 5:
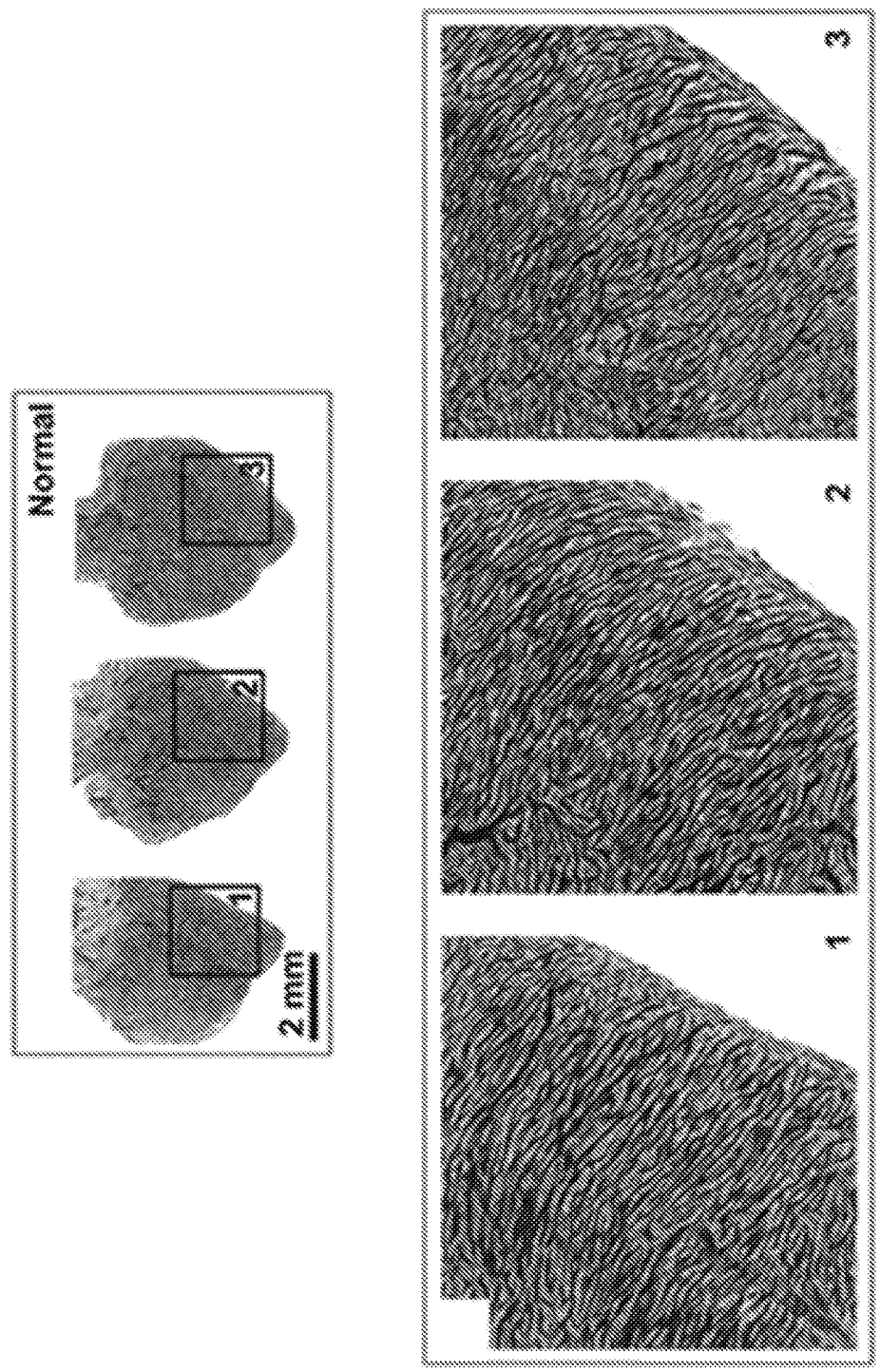
FIG. 5 includes SLIME images of 3 normal day 9 quail hearts with normal vasculature patterns.
Figure 6:
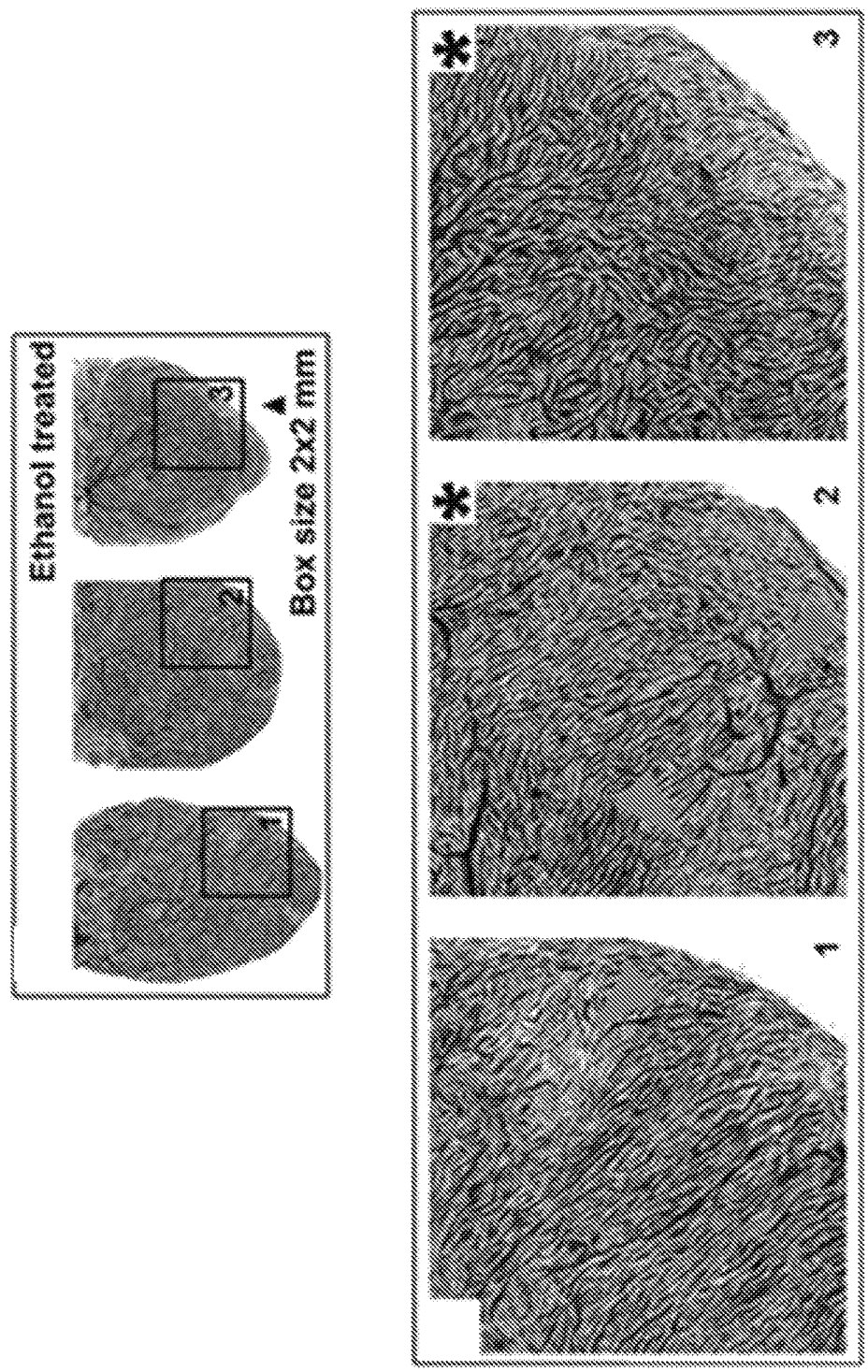
FIG. 6 includes SLIME images of E9 quail hearts exposed to ethanol during gastrulation with abnormal vasculature patterns.

In some disease models, microvascular phenotypes at the organ level can vary significantly between individuals. Investigating a small number of samples and small portions of a sample can be inconclusive or misleading. However, with traditional imaging techniques (e.g., confocal microscopy), it is often resource intensive to acquire high resolution, large FOV images for a large population. This problem can be effectively addressed with SLIME, which is capable of mapping the microvasculature at the organ level with micrometers resolution and millimeters FOV within minutes. As a demonstration, SLIME was used to produce high-resolution data of quail embryo hearts in a well-established model of fetal alcohol syndrome (FAS) with diverse cardiovascular defects (FIGS. 5 sf 6). Various atypical microvascular phenotypes (e.g., chaotic alignment, reduced vessel density, abnormal organization) were identified. These microvascular abnormalities can be subclinical, but may eventually lead to more serious heart defects.

Figure 7:
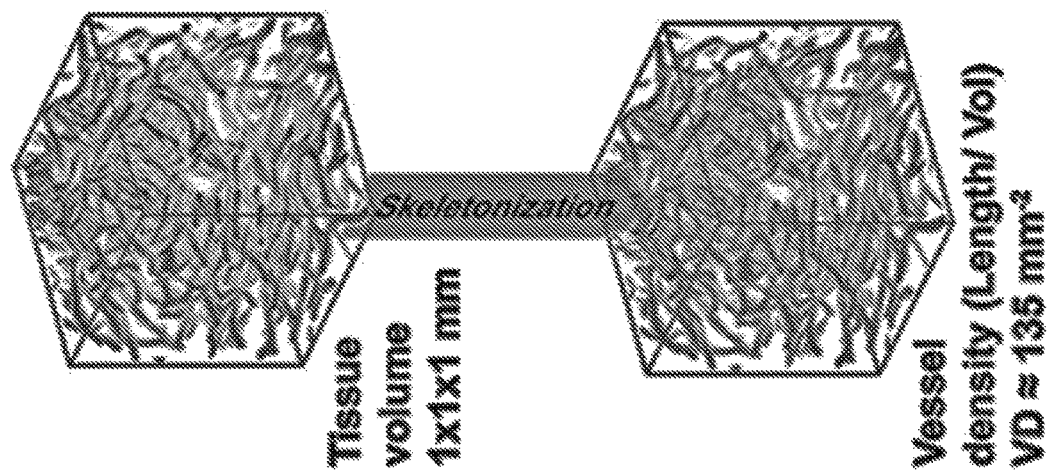
FIG. 7 shows an example vessel density (vessel length/unit volume) calculations from an arbitrarily selected 1×1×1 mm volume from the center of a normal E9 quail brain.
Figure 8:
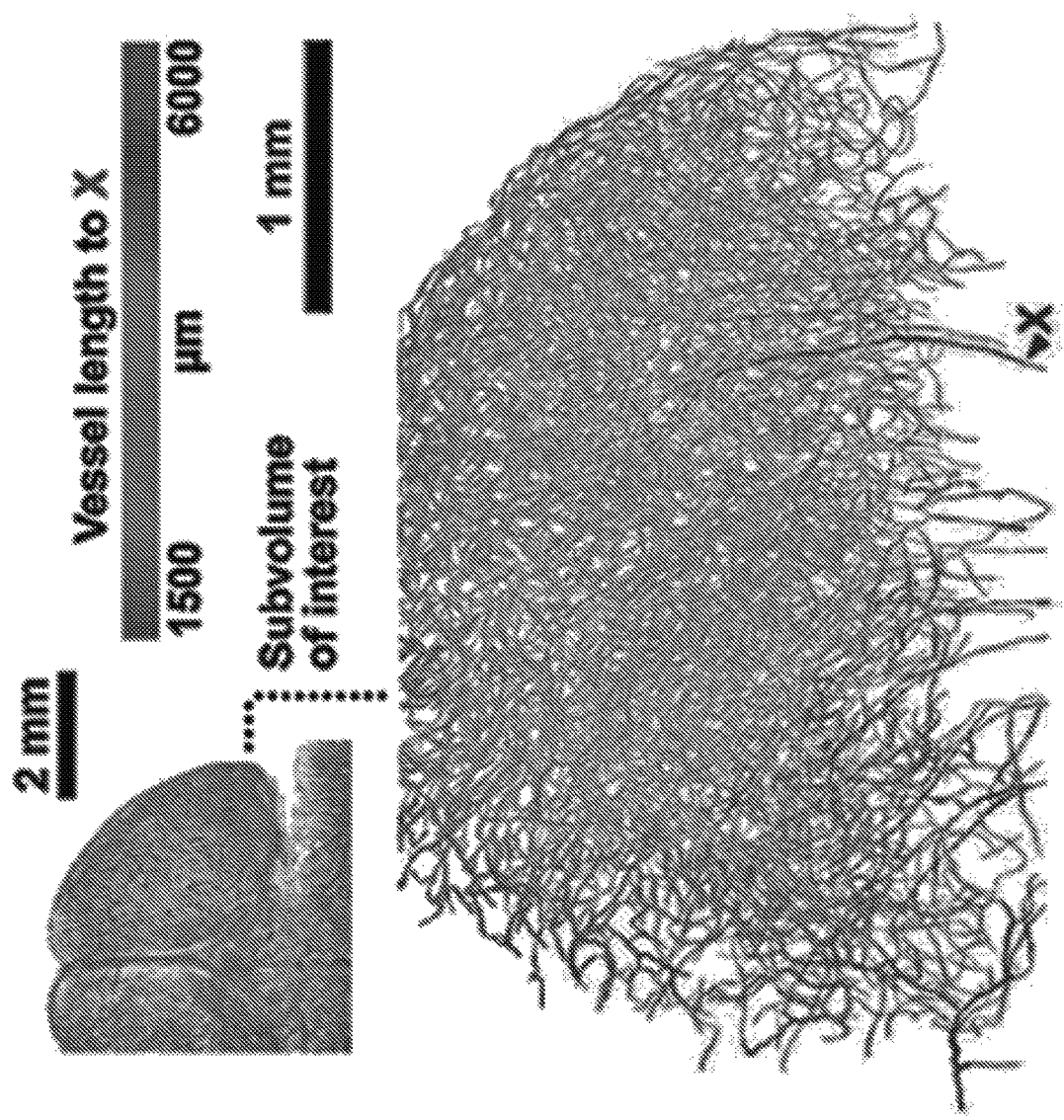
FIG. 8 is a distance map showing the connected vessel length from near the beginning of the posterior cerebral artery.
Figure 9:
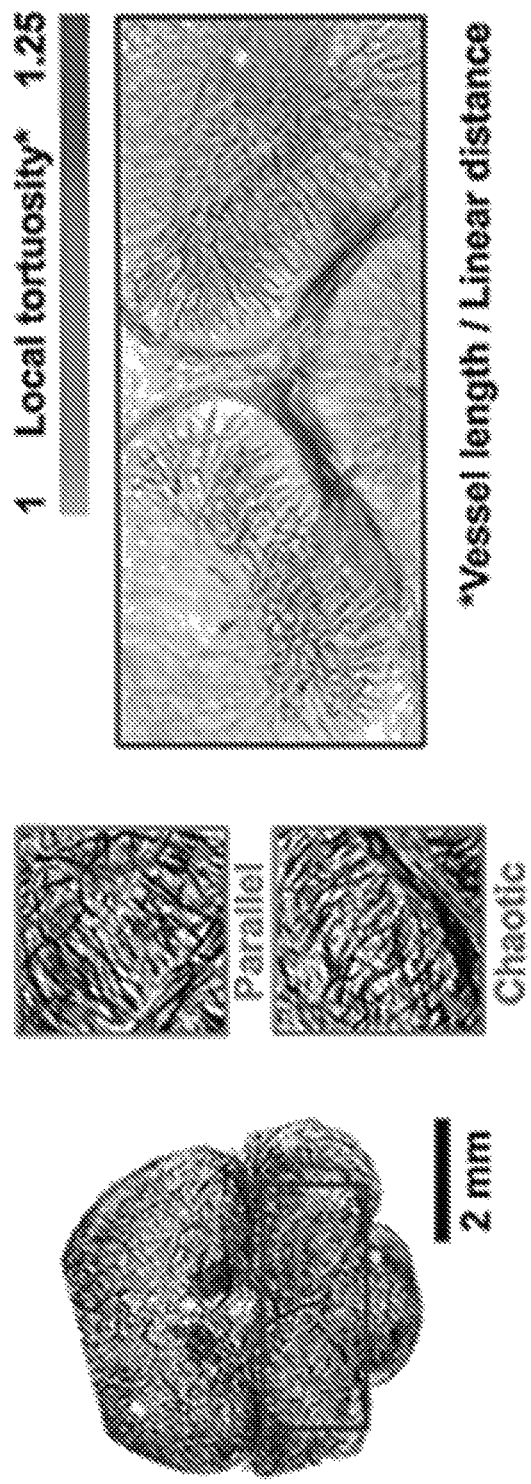
FIG. 9 shows how preliminary SLIME data includes potential abnormalities in an E9 quail brain after ethanol exposure.

Quantifying aspects of vascular morphology across an entire organ can generate numerous insights about blood perfusion and metabolism in both normal and disease states. Because of the high contrast of SLIME images and the ability to skeletonize the data, various quantitative measurements can be easily made. As a proof of concept, the quantification of SLIME images were demonstrated for a stage 36 quail embryo brain. Vessel length density (total vessel length/tissue volume (FIG. 7) and distance maps indicating vessel length to specific points of interest can be readily calculated from SLIME data using existing tools (FIG. 8). Further, quantitative measurements of SLIME images can be used as metrics to assess abnormalities. Normal embryonic quail brains show symmetrical vascular patterning between the left and right side. In the brains of the quail FAS model, SLIME data showed clear differences in local tortuosity between the left and right optical lobes (FIG. 9).

From the above description, those skilled in the art will perceive improvements, changes and modifications. Such improvements, changes and modifications are within the skill of one in the art and are intended to be covered by the appended claims.

The following is claimed:

1. A method comprising:
    perfusing a contrast agent through vasculature of a tissue sample, wherein the contrast agent comprises a colloid and a dispersant;
    treating the vasculature of the tissue sample with a molecule that cross links with at least a portion of the dispersant to form a sticky, non-Newtonian polymer that prevents leakage of the contrast agent out of the vasculature of the tissue sample; and
    immersing the tissue sample in a solution comprising a clearing agent.

2. The method of claim 1, further comprising recording one or more images of the tissue sample in the solution comprising the clearing agent.

3. The method of claim 2, wherein the one or more images are optical coherence tomography (OCT) images and the contrast agent is an OCT contrast agent.

4. The method of claim 3, wherein the colloid comprises metal nanoparticles.

5. The method of claim 4, wherein the metal nanoparticles comprises $TiO_2$.

6. The method of claim 1, wherein the dispersant comprises poly vinyl alcohol/acetate (PVA) and the molecule that cross-links with the portion of the dispersant cross-links with the PVA.

7. The method of claim 6, wherein the molecule that cross-links with the PVA is boric acid.

8. The method of claim 7, wherein the solution comprising the clearing agent further comprises boric acid to further prevent leakage of the contrast agent from the tissue sample.

9. The method of claim 1, wherein the vasculature comprises perfusable connected vessels or lumen in the tissue sample.

10. The method of claim 9, wherein the tissue sample comprises blood vessels, lymph tubes, or digestive tract.

11. The method of claim 1, wherein the vasculature of the tissue sample exhibits a high contrast with the tissue sample in the one or more images.

12. The method of claim 1, further comprising performing an image processing procedure on the one or more images, wherein the one or more images are optical coherence tomography (OCT) images.

13. The method of claim 12, wherein the image processing procedure comprises one or more of:
 applying a multi-iterative three-dimensional (3D) median filter to data related to the one or more OCT images to reduce speckle noise;
 applying coherence-enhanced diffusion filtering to reduce noise and improve vessel continuity in the data related to the one or more OCT images;
 improving image contrast and intensity uniformity by background subtraction and/or 3D unsharp filtering of the data related to the one or more OCT images; and
 segmenting the data related to the one or more OCT images through intensity thresholding and skeletonizing the segmented data related to the one or more OCT images into 3D graph data for quantitative analysis.

14. The method of claim 1, wherein the tissue sample is affected by the clearing agent and the contrast agent is not affected by the clearing agent, thus enhancing contrast between the vasculature of the tissue sample and the tissue sample.

15. The method of claim 1, further comprising assessing whether a disease state exists in the tissue sample based on analyzing the one or more images of the tissue sample.

16. The method of claim 1, wherein the analyzing further comprises quantifying aspects of morphology of the vasculature in the tissue sample.

* * * * *